United States Patent [19]

Rescalli et al.

[11] 4,020,114

[45] Apr. 26, 1977

[54] PROCESS FOR SEPARATING BUTADIENE FROM $C_4$ HYDROCARBONS STREAMS OBTAINED BY STREAM-CRACKING

[75] Inventors: Carlo Rescalli; Alessandro Ginnasi, both of San Donato Milanese, Italy

[73] Assignee: Snam Progetti S.p.A., San Donato, Milanese, Italy

[22] Filed: May 21, 1975

[21] Appl. No.: 579,714

[30] Foreign Application Priority Data

May 21, 1974 Italy .................................. 23008/74

[52] U.S. Cl. ..................... 260/681.5 R; 260/614 A
[51] Int. Cl.² ........................................... C07C 7/00
[58] Field of Search ............... 260/681.5 R, 614 A, 260/683 R

[56] References Cited

UNITED STATES PATENTS

| | | | |
|---|---|---|---|
| 1,968,601 | 7/1934 | Edlund et al. | 260/614 A |
| 2,480,940 | 9/1949 | Leum et al. | 260/614 A |
| 3,119,766 | 1/1964 | Voltz | 260/614 A |
| 3,423,385 | 1/1969 | Bebb et al. | 260/681.5 R |
| 3,784,626 | 1/1974 | Ginnasi et al. | 260/681.5 R |
| 3,846,088 | 11/1974 | Brown et al. | 260/614 A |

FOREIGN PATENTS OR APPLICATIONS

| | | | |
|---|---|---|---|
| 957,000 | 4/1964 | United Kingdom | 260/614 A |
| 1,176,620 | 1/1970 | United Kingdom | 260/614 A |

*Primary Examiner*—Winston A. Douglas
*Assistant Examiner*—John F. Niebling
*Attorney, Agent, or Firm*—Ralph M. Watson

[57] ABSTRACT

The present invention is directed to a process for the separation of butadiene from a stream-cracked $C_4$ hydrocarbon stream by a sequential etherification of isobutylene and the acetylenic compounds that is followed by a distillation step.

12 Claims, 1 Drawing Figure

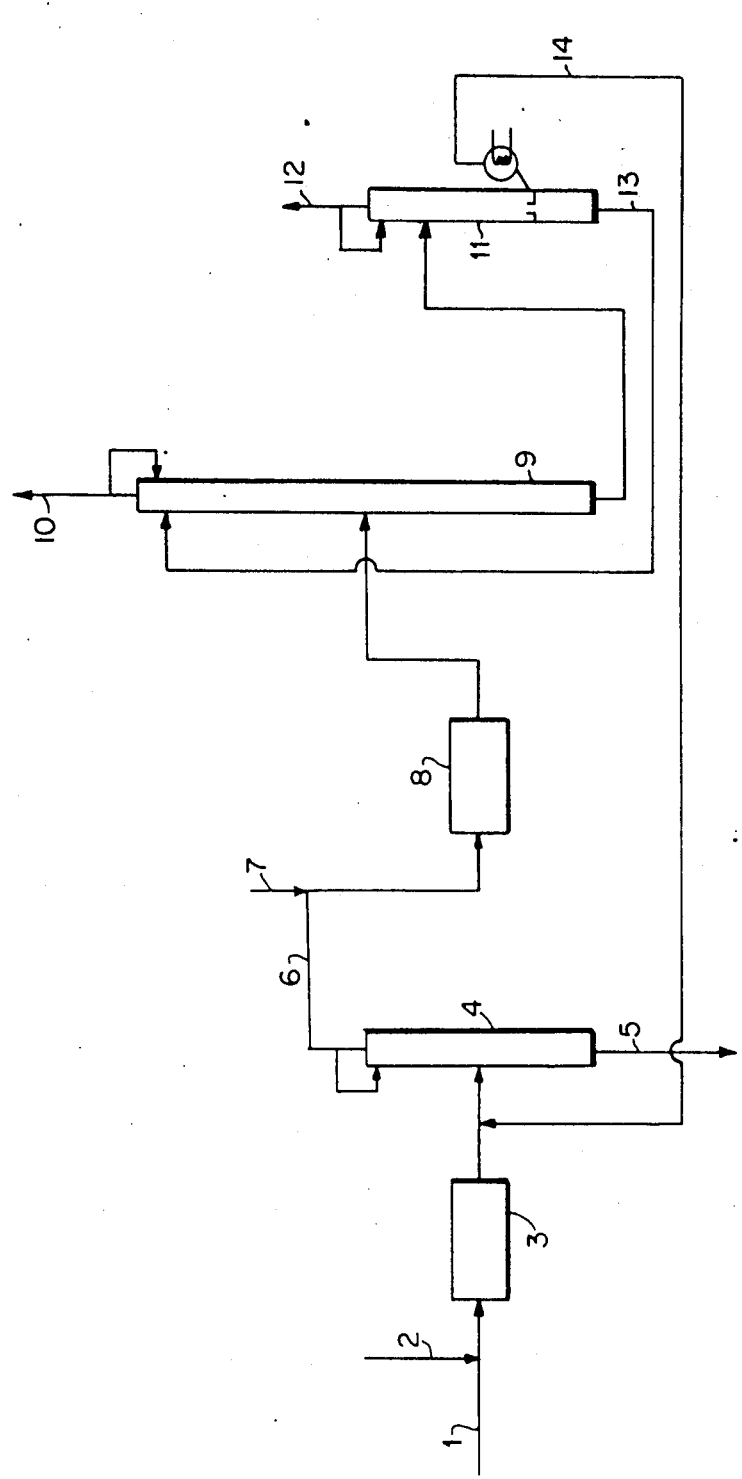

PROCESS FOR SEPARATING BUTADIENE FROM C₄ HYDROCARBONS STREAMS OBTAINED BY STREAM-CRACKING

The present invention relates to a process for separating butadiene from $C_4$ hydrocarbon stream obtained by stream-cracking.

It is known that the $C_4$ stream coming from stream-cracking is presently the main source of the butadiene utilized in the industry as polymer and/or copolymer substitutive of natural rubber; a typical composition of said stream is the following one:

| | |
|---|---|
| $C_4$ saturated hydrocarbons | ~ 6% by weight |
| $C_4$ linear olefinic hydrocarbons | ~ 28% by weight |
| Isobutylene | ~ 28% by weight |
| Butadiene | ~ 37% by weight |
| Acetylenic compounds | ~ 1% by weight |

It is also known that "polymerization grade" butadiene must present determined purity requirements and in particular a. it must have a purity $\geq$ 99.5% by weight b. the content of acetylenic compounds must be lower than 50 ppm by weight.

Presently the recovery of butadiene from the $C_4$ stream coming from stream-cracking is carried out mainly by extraction in presence of suitable solvents as dimethylformamide, N-methylpyrolidone, acetonytrile, formylmorpholine.

In practice the separation of butadiene comprises the following steps:

1. eliminating by extractive distillation or liquid-liquid washing or by gas-liquid washing n-butane, isobutane, 1-butene, isobutylene, 2 butene trans and 2 butene cis (compounds less polar than butadiene).

2. eliminating by extractive distillation 1 butyne, vinyl acetylene, diacetylene (compounds more polar than butadiene) and a portion of the propyne amount.

3. eliminating by rectification the remaining portion of propyne.

The main problems which have to be solved in the recovery of butadiene according to the aforesaid scheme are:

reducing to the lowest value the amount of solvent utilized for the separation of the less polar compounds since said amounts remarkable influences the operative costs (steam consumption for heating the solvent) and plant costs (oversizing of columns and apparatuses necessary to the partial recovery of the sensible heat of the solvent in order to minimize running costs)

avoiding high concentrations of acetylenic compounds since, being in particular vinylacetylene and diacetylene highly unstable compounds, there is a possibility to have otherwise extremely risky situations for the plant (it is known that butadiene extraction plants have suffered great damages because of explosions due to insufficiencies which have brought the concentration of the aforesaid compounds to values outside the safety limits).

In order to avoid what above said normally rather remarkable losses of butadiene must be tolerated (the acetylenic streams are removed from the cycle at a low concentration level).

It has been surprisingly found that it is possible to recover butadiene both with lower costs and with a higher working safety simply by etherifying isobutene and acetylenic compounds.

Object of the present invention is a process for separating butadiene from hydrocarbon streams containing the same consisting in etherifying isobutylene with methanol or another alcohol in presence of an acid ion-exchange resin and in etherifying acetylenic compounds with methanol or another alcohol in presence of the same or of a different acid ion-exchange resin which in this case however contains also mercuric ions.

The isobutylene etherification can be carried out either before the etherification of the acetylenic compounds in a different reactor (in total 2 reactors) or contemporaneously in the same reactor.

The obtained ethers and the other compounds are then removed from butadiene by distillation operations.

As acid ion-exchange resin we may choose any of the ones available on the market but preferably use has to be made of a resin containing sulphonic groups ($-SO_3H$) or carboxylic groups.

Still more particularly said resin can have a polystyrenic or polyphenolic matrix.

The numeric ions can be added to the resin in the form of mercury salts for instance in particular in the form of Hg nitrate; the content of mercuric ions of the resin may be also lower than the total cationic capacity of the resin.

With reference to FIG. 1 a particular embodiment of the process object of the present invention will now be described, said embodiment being to be considered in any case as not restrictive of the invention.

Said particular embodiment forsees:

etherifying with methanol 2 most of isobutylene (85 + 95% of isobutylene present in the feed stream 1 in reactor 3 by working in presence of an acid ion-exchange resin; the reaction is effected at a temperature in the range of from 20° to 80° C with a working pressure at least equal to the vapour pressure of the feed mixture and with LHSV (space velocity expressed as volumes of liquid per hour and per volume of catalyst) in the range of from 2 to 30.

recovering the formed methyl ter-butyl ether 5 from the bottom of the distillation column 4.

etherifying with methanol 7 isobutene remained in the hydrocarbon stream 6 and all acetylenic compounds present in the same stream 6 in reactor 8, by working in presence of an acid ion-exchange resin to which mercuric ions have been added; the temperature in said second reactor is in the range of from 20° to 80° C with a working pressure at least equal to the vapour pressure of the feed mixture and with LHSV in the range of from 1 to 30.

separating linear saturated and olefinic hydrocarbons from butadiene by extractive distillation in column 9. The saturated and olefinic hydrocarbons are discharged as overhead product through 10.

A selective solvent for butadiene and ethers is used.

Selective solvents to be quoted are N-formyl morpholine, N-methyl pyrrolidone, dimethyl formamide, acetonitrile, dimethylacetamide, N-methylimidazole, 1.3 imidazolydin 2 one, βmetoxypropionitrile.

separating in stripping column 11 butadiene 12 from extractive solvent 13 utilized in the preceding column.

From the vapour phase of an intermediate plate of 11 a stream 14 is discharged rich of the etherification products which, formed in 8, have been fed to 9; said products are removed from the cycle by recycling the stream itself to distillation column 4.

An example will now be given in order to illustrate in a better way the invention without restricting in any case the same.

EXAMPLE 1

Reference will be made to the enclosed drawing. Together with 16.7 kg/h of methanol 2 (isobutene/methanol = 1.0 mole/mole) to the reactor 3 we fed kg/h of a $C_4$ feed 1 constituted by:

| | | |
|---|---|---|
| n-butane | = | 3.73% by weight |
| iso-butane | = | 0.86% by weight |
| 1-butene | = | 16.44% by weight |
| isobutene | = | 29.19% by weight |
| 2 butene trans | = | 5.89% by weight |
| 2 butene cis | = | 4.29% by weight |
| 1-3 butadiene | = | 39.07% by weight |
| Propyne | = | 0.03% by weight |
| Vinyl acetylene | = | 0.40% by weight |
| 1 butyne | = | 0.10% by weight |

Reactor 3 worked at the following conditions:

| | |
|---|---|
| Temperature: | 60° C |
| Pressure: | 10 ata |
| LHSV | 5 |
| Resin | Amberlist 15 |

The stream leaving the reactor was fed to column 4 working at the following conditions:

| | | |
|---|---|---|
| Overhead pressure | = | 4 ata |
| Plates | = | 30 |
| Reflux ratio (L/D) | = | 1 |

While the bottom stream 5 containing all formed methyl terbutyl ether was removed from the cycle, stream 6 discharged as overhead product was fed to reactor 8 together with 0.35 kg/h of methanol 7; reactor 8 worked at the following conditions:

| | |
|---|---|
| Temperature: | 40° C |
| Pressure: | 7 ata |
| LHSV: | 5 |
| Resin: | Amberlist 15 to which $Hg^{++}$ ions were added in such amount to neutralize 20% of the $SO_3H$ groups of the resin. |

The stream leaving reactor 8 was fed to extrative distillation column 9 to the top of which contemporaneously a stream 13 was sent constituted by 900 kg/h of extrative solvent (Formyl morpholine-water = 95/5 by weight).

The working conditions of 9 were:

| | | |
|---|---|---|
| Overhead pressure: | | 4 ata |
| L/D | = | 1.2 |
| Plates | = | 90 |

As overhead product a stream 10 was discharged constituted by:

| | | |
|---|---|---|
| n-butane | = | 3.73 kg/h |
| isobutane | = | 0.86 kg/h |
| 1 butene | = | 16.43 kg/h |
| 2 butene trans | = | 5.85 kg/h |

| | | |
|---|---|---|
| 2 butene cis | = | 4.14 kg/h |
| 1.3 butadiene | = | 0.35 kg/h |

The bottom stream was fed to column 11 working at the following conditions:

| | | |
|---|---|---|
| Pressure: | | 1.2 ata |
| L/D | = | 1 |
| Plates | = | 30 |

While from the 5th plate (vapour phase) from the bottom a stream 14 was discharged which (after condensation) was recycled to column 4 and which contained, besides methyl ter-butyl ether also all vinyl ethers formed in 8 and methanol in excess over that necessary to the reaction, from the top a stream 12 of butadiene at the desired purity (38.0 kg/h) was discharged.

Solvent 13 discharged from the bottom of 11 was utilized again a extractive solvent in column 9.

What we claim is:

1. A process for separating butadiene from $C_4$ hydrocarbon streams obtained by steam cracking containing, besides butadiene, $C_4$ linear saturated and olefinic hydrocarbons, isobutylene and acetylenic compounds characterized in that isobutylene is etherified in a first reactor with methanol or another alcohol in presence of an acid ion exchange resin, the acetylenic compounds are etherified with methanol or another alcohol in a second reactor in presence of the same or of different acid ion exchange resin containing mercuric ions in amount also lower than that of the acid ions and thereafter subjecting to distillation operations the ether containing mixture for separating both the saturated and olefinic hydrocarbons and said ethers from butadiene.

2. A process as claimed in claim 1 wherein the etherification of isobutylene and the etherification of the acetylenic compounds are carried out in the same reactor.

3. A process for separating butadiene from $C_4$ hydrocarbon streams obtained by steam cracking containing, besides butadiene, $C_4$ linear saturated and olefinic hydrocarbons, isobutylene and acetylenic compounds characterized in that 85% to 95% by weight of fed isobutylene is etherified with methanol in a first reactor in presence of an acid ion-exchange resin, the produced methyl ter-butyl ether is separated by distillation in a column, isobutylene remaining in the hydrocarbon stream and all acetylenic compounds in the same stream are then etherified with methanol in a second reactor in presence of an acid ion-exchange resin to which mercuric ions have been added, $C_4$ saturated and olefinic hydrocarbons are removed as overhead product from a subsequent extractive distillation column working with a solvent selective for butadiene and ethers, obtaining as bottom product a mixture of solvent, ethers and butadiene from which, by stripping in a column, butadiene is separated as overhead product, the ethers being discharged in vapour phase from an intermediate plate of the same column and sent again to the column effecting the separation of ter-butyl ether, the recovered solvent being utilized again in the extractive distillation column.

4. A process as claimed in claim 1 characterized in that the acid ion-exchange resin contains sulphonic groups (-SO$_3$H).

5. A process as claimed in claim 1, characterized in that the acid ion-exchange resin contains carboxylic groups.

6. A process as claimed in claim 1 characterized in that the acid ion-exchange resin has polystyrene matrix.

7. A process as claimed in claim 1 characterized in that the acid ion-exchange resin has a polyphenolic matrix.

8. A process as claimed in claim 1 wherein the mercuric ions are added in the form of mercuric salts, particularly as mercury nitrate.

9. A process as claimed in claim 1 characterized in that the reaction in the first reactor is carried out at a temperature in the range of from 20° to 80° C with a working pressure at least equal to the vapour pressure of the feed mixture and LHSV in the range of from 2 to 30.

10. A process as claimed in claim 1 wherein the reaction in the second reactor is carried out in the range of from 20° to 80° C with a working pressure at least equal to the vapour pressure of the feed mixture and with LHSV in the range of from 1 to 30.

11. A process as claim in claim 3 wherein the separation of C$_4$ saturated and olefinic hydrocarbons is carried out by means of a liquid-liquid extraction column working with a solvent selective for butadiene and ethers.

12. A process as claimed in claim 3 wherein the solvent selective for butadiene and ethers is selected among N-formyl moropholine, N-methyl pyrrolidone, dimethylformamide, acetonitrile, dimethyl acetamide, N-methyl imidazole, 1,3 dimethyl imidazolydin 2 one and β-metoxypropionitrile.

* * * * *